United States Patent
Tran et al.

(10) Patent No.: US 10,557,105 B1
(45) Date of Patent: Feb. 11, 2020

(54) EXTRACTION SYSTEMS AND METHODS (71) Applicants: Ha Tran, Saratoga, CA (US); Bao Tran, Saratoga, CA (US)

(72) Inventors: Ha Tran, Saratoga, CA (US); Bao Tran, Saratoga, CA (US)

(73) Assignee: Bao Tran, Saratoga, CA (US)

( * ) Notice: Subject to any disclaimer, the term of this patent is extended or adjusted under 35 U.S.C. 154(b) by 0 days.

(21) Appl. No.: 16/536,491

(22) Filed: Aug. 9, 2019

(51) Int. Cl.
| | |
|---|---|
| *C11B 1/10* | (2006.01) |
| *A23L 3/375* | (2006.01) |
| *C07D 309/18* | (2006.01) |
| *C11B 1/04* | (2006.01) |
| *A23L 3/36* | (2006.01) |

(52) U.S. Cl.
CPC ............ *C11B 1/104* (2013.01); *C07D 309/18* (2013.01); *C11B 1/04* (2013.01); *C11B 1/106* (2013.01); *A23L 3/36* (2013.01); *A23L 3/375* (2013.01); *Y10S 241/37* (2013.01)

(58) Field of Classification Search
CPC ... C11B 1/10; C11B 1/04; C11B 1/106; C11B 1/104; C07D 309/18; A23L 3/36; A23L 3/375; Y10S 241/37
See application file for complete search history.

(56) References Cited

U.S. PATENT DOCUMENTS

| | | | | |
|---|---|---|---|---|
| 4,090,669 | A * | 5/1978 | Lermuzeaux | A23N 5/00 241/8 |
| 6,409,841 | B1 | 6/2002 | Lombard | |
| 6,807,799 | B2 | 10/2004 | Reaux | |
| 7,151,125 | B2 | 12/2006 | Williams | |
| 7,678,931 | B2 * | 3/2010 | Fichtali | A61K 36/00 554/20 |
| 7,681,388 | B1 | 3/2010 | Hinds | |
| 8,902,413 | B2 | 12/2014 | Ulmman | |
| 9,002,071 | B2 | 4/2015 | Nakagome | |
| 9,309,401 | B2 | 4/2016 | Mohanty | |
| 9,427,423 | B2 * | 8/2016 | Swanick | A61K 9/10 |
| 9,850,379 | B2 | 12/2017 | Li | |
| 9,873,813 | B2 * | 1/2018 | Cornish | F26B 1/00 |
| 9,987,567 | B1 | 6/2018 | Ko | |
| 10,011,804 | B2 * | 7/2018 | Mancosky | C11B 1/04 |

(Continued)

FOREIGN PATENT DOCUMENTS

| | | | | |
|---|---|---|---|---|
| CN | 106544152 A | * | 3/2017 | C11B 1/04 |
| WO | PCT/US2017/03885 | | 12/2017 | |

OTHER PUBLICATIONS

CN106544152 (A), Zhang Jie, Method for extracting tea seed oil from oil-tea camellia seeds, 2017, English translation, 6 pages (Year: 2017).*

(Continued)

Primary Examiner — Yate' K Cutliff
(74) Attorney, Agent, or Firm — Tran & Associates (57) ABSTRACT

System and methods are disclosed to process a biomass with a cryogenic fractionator to decimate the biomass into small portions; a holding tank to receive liquid and the small portions of biomass; a cavitator to generate shock waves and pressure variations, wherein the shock waves and pressure variations are to the biomass and the liquid to separate oil from the biomass; a sensor to determine when oil concentration exceeds a threshold; and a valve to transfer the oil and liquid to an oil tank when the threshold is met.

10 Claims, 3 Drawing Sheets

| |
|---|
| Harvest Hemp Plants (2) |
| Separate parts of the Hemp into buds, leaf, stalk, and root (3) |
| Cryogenically freeze the parts of the plant and fractionalize the parts into small parts (4) |
| Extract oil (5) |
| Post extraction, convert hemp biomass into biocomposite materials (9) |

(56) References Cited

U.S. PATENT DOCUMENTS

| | | | |
|---|---|---|---|
| 10,059,632 B2 | 8/2018 | Li | |
| 10,101,328 B1 | 10/2018 | Amini | |
| 10,119,027 B2 | 11/2018 | Chen-sarkanen | |
| 10,179,744 B2 | 1/2019 | Le | |
| 2004/0040680 A1 | 3/2004 | Iwasaki | |
| 2005/0150005 A1 | 11/2005 | Pang | |
| 2006/0282274 A1 | 12/2006 | Bennett | |
| 2008/0075900 A1 | 3/2008 | Hepworth | |
| 2012/0046394 A1* | 2/2012 | Lu | C08K 7/02 524/9 |
| 2013/0322700 A1 | 12/2013 | Sugasawa | |
| 2014/0285673 A1 | 9/2014 | Hundley | |
| 2015/0291784 A1 | 10/2015 | Ruef | |
| 2016/0307448 A1 | 10/2016 | Salnikov | |
| 2017/0051231 A1* | 2/2017 | Mancosky | C11B 1/02 |
| 2017/0333505 A1 | 11/2017 | Gharib | |
| 2018/0209448 A1 | 7/2018 | Lee | |
| 2018/0070586 A1 | 8/2018 | Kim | |

OTHER PUBLICATIONS

Tewari, V. K., A. A. Kumar, S. P. Kumar, V. Pandey, and N. S. Chandel. 2013. Estimation of plant nitrogen content using digital image processing. Agric Eng Int: CIGR Journal, 15(2): 78-86.

Muñoz-Huerta, et al, A Review of Methods for Sensing the Nitrogen Status in Plants: Advantages, Disadvantages and Recent Advances, Sensors Aug. 16, 2013, 13, 10823-10843; doi:10.3390/s130810823.

Smart Fertilize Plan Management, Dec. 2018.

Kuhnemund et al, Targeted DNA sequencing and in situ mutation analysis using mobile phone microscopy, Nature (Jan. 17, 2017) Communications | 8:13913 | DOI: 10.1038/ncomms13913 |www.nature.com/naturecommunications.

CapGemini, Digital Agriculture Bytes against Hunger Translating local and personal approaches of digital agriculture (2018).

\* cited by examiner

FIG. 1

| |
|---|
| Harvest Hemp Plants (2) |
| Separate parts of the Hemp into buds, leaf, stalk, and root (3) |
| Cryogenically freeze the parts of the plant and fractionalize the parts into small parts (4) |
| Extract oil (5) |
| Post extraction, convert hemp biomass into biocomposite materials (9) |

| |
|---|
| Feed hemp biomass to a conveyor |
| Hemp is broken into small particles, and oil such as THC is extracted and processed |
| Post extraction hemp biomass is processed using steam explosion, among others |
| Treat biomass by dilute acid hydrolysis |
| Treat unreacted lignocellulostic component of acid hydrolyzed biomass by alkaline delignification |
| Resulting hemp biomass is converted into plastic |

FIG. 4

EXTRACTION SYSTEMS AND METHODS

BACKGROUND

The present system relates to farming systems and methods.

CBD (Cannabidiol) is a compound that has shown promise in a variety of medical applications, from pain relief to relieving anxiety, and many other ailments in between. A major benefit to CBD is that it doesn't contain THC, which is the compound that makes users high, so this makes CBD an ideal medication for children.

There are many ways to extract the oil from the plant and make cbd oil. Apeks Supercritical systems use CO2 as a solvent to extract the oil. The solvent is considered a cleaner, purer form of extraction because there is no residue after extraction.

To isolate the individual compounds (CBD being one of them), the extracted oil needs to be distilled after extraction. The first step is a process called Winterization, followed by Short Path Distillation.

Winterization is the process to remove undesirable elements that were extracted from the plant, for example fats, waxes and lipids. This process is only needed when the oil was extracted at high pressure/high temperature (supercritical) because this intense extraction pulls everything from the plant, including material you don't want in the final product. The extracted oil is effectively crude oil, which needs refining. Once extracted, the mixture is combined with 200 proof alcohol and stirred vigorously until completely mixed. It's then placed in a deep freezer overnight. In the morning, the mixture looks cloudy and is ready for filtration. One way to filter out the fats, etc. is to run it through a filter paper into an extraction jar. A common piece of equipment for this is a Buchner Funnel. Once it's been filtered to satisfaction and the undesirable elements have been removed, it's time to remove the alcohol. This is done using heat. The extraction is warmed and as its warmed, the alcohol evaporates since the boiling point of alcohol is lower than the oil. The removed alcohol can then be reused on a different batch of crude oil. To further refine the extract, and to isolate the CBD, the oil goes through Short Path Distillation. This works in much the same way as Winterization in that the extract is heated and each compound is then separated because each one has a different boiling point. In this way, each compound is isolated and can be used by itself.

SUMMARY

In one aspect, system and methods are disclosed to process a biomass with a cryogenic fractionator to decimate the biomass into small portions; a holding tank to receive liquid and the small portions of biomass; a cavitator to generate shock waves and pressure variations, wherein the shock waves and pressure variations are applied to the biomass and the liquid to separate oil from the biomass; a sensor to determine when oil concentration exceeds a threshold; and a valve to transfer the oil and liquid to an oil tank when the threshold is met.

Implementations may include one or more of the following. A chemical processor can extract oil from the crop and thereafter using the crop as a bio-material. The oil comprises tetrahydrocannabinol (THC) or cannabidiol (CBD) from the liquid. A temperature sensor can detect temperature of the liquid, wherein cryogen is applied to the liquid for cooling. A sensor can detect oil concentration in the liquid. The oil is removed once the oil concentration exceeds a threshold, wherein the liquid is water, comprising a boiler to boil off water, a centrifuge, or a nano filter to remove oil from the water. A second oil extraction stage for tetrahydrocannabinol (THC) or cannabidiol (CBD) using ethanol and cryogenic cooling with LN2 or CO2. A crop biomass into a bioplastic or a biocomposite material or a building material. The liquid can be water or a solvent.

In another aspect, composites that retain the natural antibacterial properties of hemp can be used to kill several types of surface bacteria including *E. coli*. Such products can be used in medical facilities, kitchen supplies, plant or calf toys, exercise mats etc.

Advantages of the system may include one or more of the following. The efficiency yield of extraction in the present invention is substantially greater than prior art extraction techniques and methods, the cost is lower, and the present system may be scaled up easily to virtually any commercial production rate. The system can thus be used to extract desirable compounds such as CBD, THC and oils for medicinal or other legal uses on a commercial scale. Moreover, the use of controlled cavitation can provide a better result at nearly any commercial volume. Cavitation also produces more energetic shock waves than ultrasound in the sense that higher energy pressure variations are generated by the cavitation events. This may also result in faster and higher yield. Extraction through controlled cavitation can easily incorporate plant and other lignocellulosic material because of its inherent low shear and relatively large clearances within the cavitation zone. The system provides improved process efficiencies (in time, operating costs, and/or capital costs), which results in improved product quality, yield and/or raw material savings. The system provides more effective and efficient mixing and increase transfer rate while eliminating or reducing process downtime from maintenance requirements. Low power mixing is achieved by the system, ensuring an environmentally sustainable operation.

DESCRIPTION

Figure 1:
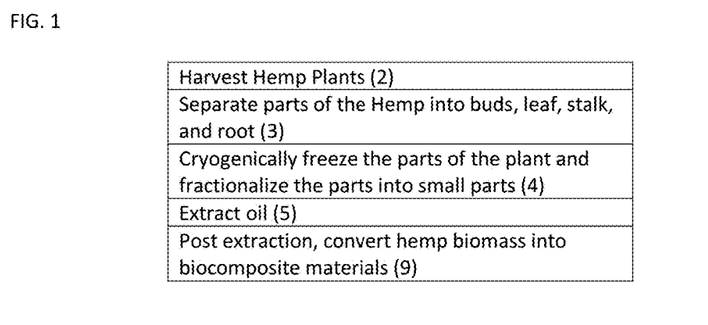
FIG. 1 shows an exemplary process to extract oil from hemp.

FIG. 1 shows an exemplary process to extract oil. The process includes:

Harvest Hemp Plants (2)

Separate parts of the Hemp into buds, leaf, stalk, and root (3)

Cryogenically freeze the parts of the plant and fractionalize the parts into small parts (4)

Extract oil (5)

Post extraction, convert hemp biomass into biocomposite materials (9)

Harvesting System

Figure 2:
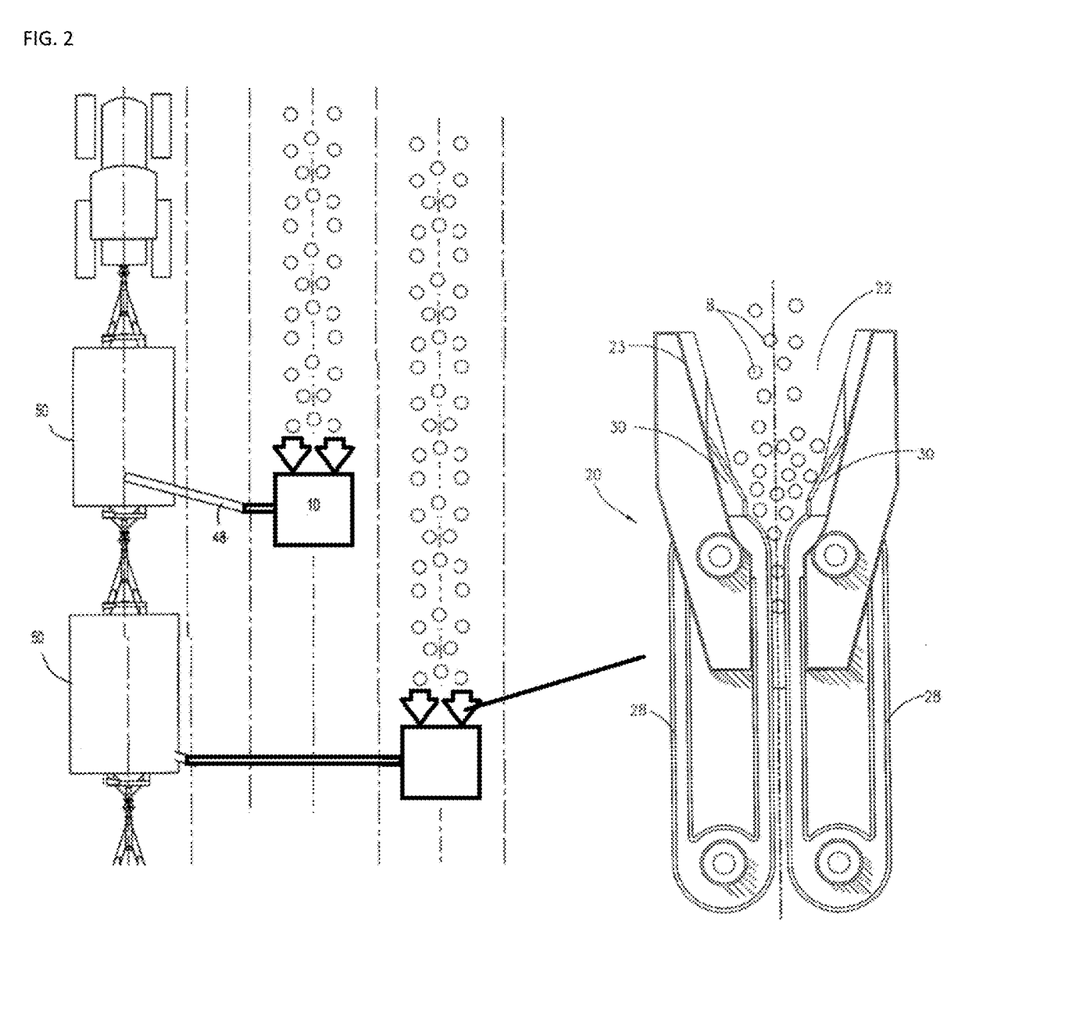
FIG. 2 shows an exemplary process to harvest hemp.

FIG. 2 shows an exemplary in-place oil extraction system. The system includes a vehicle/tractor that pulls one or more trailers 50 to extract oil. Each trailer 50 operates with a unit 10 that captures the hemp, identifies and severs parts of the hemp plant. The hemp stalks are then deposited into a processing chamber in trailer 50 that extracts oil from the hemp. After extraction, the post-extraction hemp biomass can be converted into bio-plastics or other suitable materials as detailed herein. While hemp processing is detailed, the description can be applied to any suitable crops.

Turning now to FIG. 2, the operation of the front end unit 10 is detailed. The hemp enters an entrance 22, then the buds are first identified by computer vision and are severed by laser cutting or water cutting, where the cutter can be moved on a robot platform for precision cutting. Blowers/vacuum ports selectively pickup parts into flower bins and leaf bins. Then the leaves are severed, and then the stalk (8) is processed. Positioned within each harvest chamber, at selected locations, are a plurality of stalk cutting robot arms with cutters. Each cutter can be a laser or hydraulic jets for delivering needle-like streams of water or other desired fluid at high pressure for cutting the parts of the stalks.

Within each harvest chamber is a defoliation blower assembly with a plurality of adjustable blower nozzles, positioned at selected locations along each of the sidewalls. The blower nozzles are connected to blowers for directing high velocity streams of air through the nozzles, via blower ducts, onto the stalks. These high velocity air streams remove the stems and leaves from the stalks. The nozzles and blowers use the image recognition controller of FIG. 2 connected to the operator control station for adjusting by remote control the velocity and direction of air flow from the nozzles, both in azimuth and angle, to create as desired both direct air flow and cyclone air flow in the harvest chamber to facilitate the defoliation of specific parts of the stalks such as the flowers and leaves. Also positioned within each harvest chamber assembly is a vacuum assembly comprised of a plurality of vacuum or suction ports connected to a suction motor, via suction ductwork, for removing by vacuum the leaves and flowers from the harvest chamber and for delivering the defoliated flowers/leaves and stems to the foliage collection assembly. The suction ports are positioned at the base of the sidewalls and may be positioned at other desired locations along the chamber sidewalls to facilitate removal of the defoliated flowers and leaves, stems and other debris from the harvest chamber as defoliation takes place.

As shown in FIG. 2, the stalks 8 are gathered in the entrance 22 of a harvest chamber 20 as the harvester moves along the row of hemp stalks for cutting and processing. Positioned in the harvest chamber 20 are a series of revolving, opposing, resilient conveyor belts that grab, hold and feed the hemp 8 through the chamber 20 in a substantially upright position. The roots are cut, and the hemp stalks are gathered into the chamber 20, the flowers are cut using robot arms and the stalks 8 are defoliated by means of the defoliation assemblies 30, which defoliates the leaves. Then, as the stalks 8 progress through the chamber 20, they are grabbed and supported by means of the revolving, opposing, resilient conveyor belts 28 and cut to desired lengths by the cutting assemblies 50. After being cut, the stalks 8 are delivered by the conveyor belts 28 to the collection bay assembly and then to a stalk discharge assembly 48 by conveyors, vacuum systems or other conveying systems for subsequent transfer to collection vehicles having collection wagons 50 in the field and then oil can be extracted on-site, with the remaining biomass delivered to a follow up location for secondary processing. Alternatively, the separated parts of the hemp plant are delivered to a grinding mill or other desired location.

One embodiment uses a harvester/extraction system. Mounted on the harvester chassis is a plurality of harvest chambers. Each harvest chamber has a V-shaped entrance for receiving a row of hemp stalks and a series of revolving resilient conveyor belts for grabbing, removing plant from soil, holding and feeding the hemp stalk through the harvest chamber in a substantially upright position. Within each harvest chamber, at selected locations, is a plurality of computer-controlled blower nozzles (adjustable both in azimuth and angle) for directing high velocity streams of air (either direct or cyclone) on to the hemp stalks to remove the stems and leaves from the stalks of sugarcane. The computer control uses the GAN type neural network to direct the blower nozzles and to cut the parts of the hemp. At the base of each harvest chamber is a plurality of lower vacuum or suction openings connected to a suction motor for removing by vacuum the leaves and stems from the harvest chamber and for delivering the leaves and stems removed to a foliage collection area having a "biomass chamber" for drying the leaves and stems.

As the hemp stalks are being cut and thereafter, they are grabbed and moved through the chamber by revolving resilient conveyor belts to a collection bay for subsequent transfer to a trailer for on-the-spot oil extraction. Preferably the cutting device for both the upper and lower cutting mechanisms are hydraulic jets for delivering needle-like streams of water or other desired fluid at high pressure for cutting the hemp into parts such as leaves, flowers, stalks, and roots, for example. The hydraulic jets are supplied by on-board water reservoirs and pumps mounted on the chassis of the harvester. Collection troughs and pumping means are provided to collect and deliver the residual fluids produced from the jets back to the reservoirs for reuse. The water used for the jets may be treated with fertilizers, insecticides, preservatives or other such chemicals as may be required to facilitate the growing, harvesting and processing of the hemp stalks. Fine grit abrasives may be added to the water or other cutting fluid to facilitate cutting. While it is thought that the harvester will best be served by cutting jets, alternative cutting devices for both the upper and lower cutting mechanisms such as cutting lasers or rotating blades could also be utilized as either the upper and lower cutting means described herein.

Immediately after cutting, major parts are identified using computer vision. The cut flowers/buds are separated using vacuum into a flower chamber. The foliage collection area is mounted toward the rear of the harvester for receiving the leaves, stems and other debris removed by vacuum from the harvest chambers.

The result of the harvest of the hemp can be used as follows. The hemp buds, also known as hemp flowers are commonly used for vaping, smoking, and baked into brownies, cookies, among others. To use the buds, decarboxylation is done by heating the hemp buds to activate the cannabinoids within, using chemistry to convert to CBD. The hemp buds are ground with an herb grinder and layered the bottom of a baking pan or sheet with the ground buds. Place in a preheated oven of 245° F. and allow the buds to bake for about an hour before removing them. To extract the CBD, the activated CBD is placed into something slippery and greasy, such as ghee, butter, or oil and cooked at low temperature. Once the bud and butter/ghee/oil have combined, the bud is strained from the butter/ghee/oil using a mesh sieve and the result is CBD infused oil that can be used for cooking.

Hemp seeds can be used for many things such as Body care, Cosmetics, Soaps, Balms, Shampoos, Lotions, Foods (such as Hemp seed hearts, EFA food supplements, Hemp protein powder, Hemp seed oil), and Industrial Products (such as Coatings, Oil paints, Solvents, Varnishes, Fuel, Printing inks), among others. The stalk of the hemp plant is where CBD oil comes from. Fourteen states within the US can legally grow and process industrial hemp and hemp seeds. A few other ways hemp stalks can be used (besides CBD oil) include: BioPlastic, Paper, Packaging, Printing, Cardboard, Newsprint, Textiles, Fine fabrics, Clothing, Shoes, Diapers, Denim, Handbags, Building materials (Fiberglass substitute, Fiberboard, Insulation, Acrylics, Industrial Textiles), and Molded parts (such as Rope, Caulking, Canvas, Netting, Tarps, Carpeting). The leaves of the hemp plant can be used too, as they are very absorbent, which makes them good for animal bedding, great for adding to compost and mulch. The roots of the hemp plant can be used as remedy for conditions such as joint pain, arthritis, eczema and fibromyalgia, and for organic compost and nutrients.

Also mounted on the chassis, for incorporation into the harvester and system, is a means for providing hydraulic or electrical power to activate a plurality of harvesting equipment, blowers, vacuums, conveyors, elevators and other accessories that may be incorporated into the harvester.

On Farm Extraction of Oils

Figure 3:
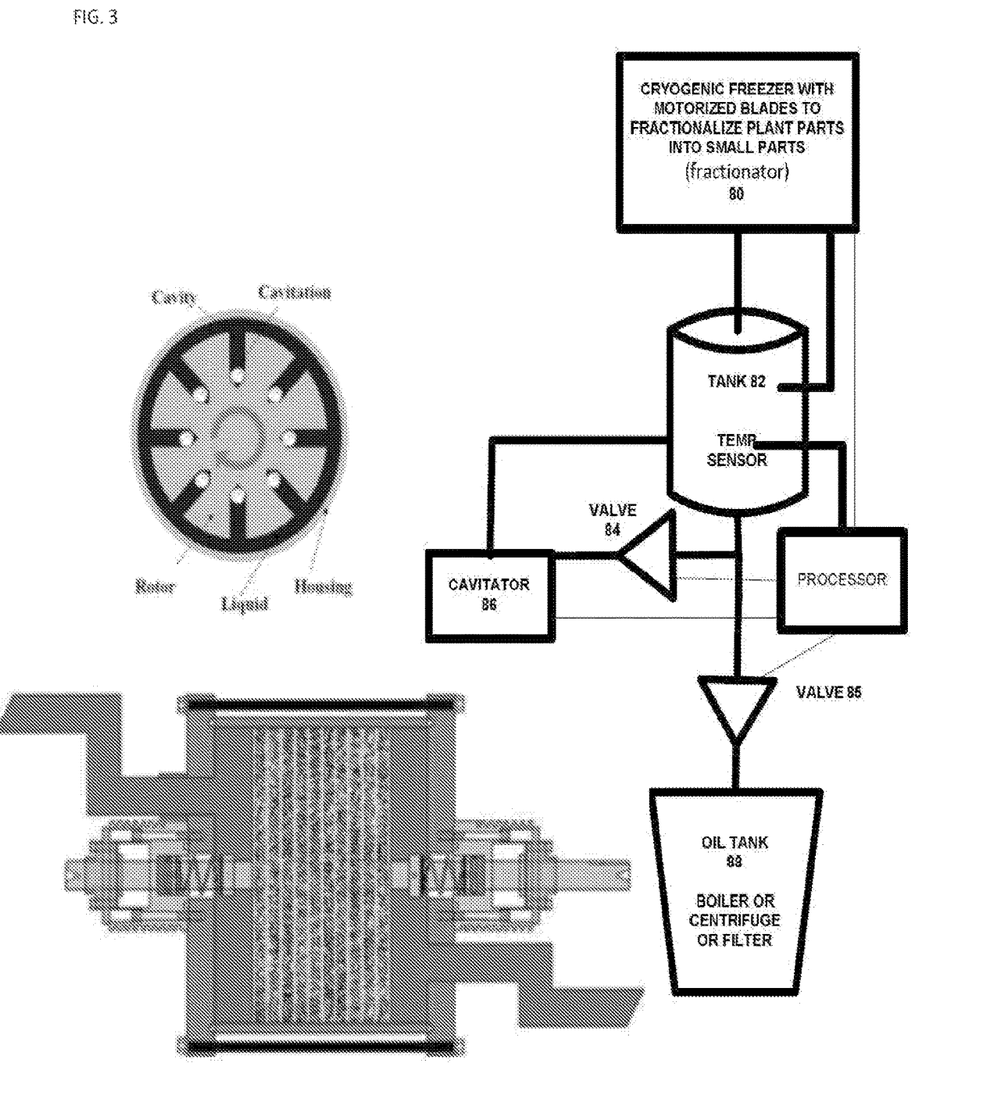
FIG. 3 shows an exemplary cavitation extraction system.

One embodiment uses water extraction of oils through cavitation. FIG. 3 shows one embodiment where the biomass is first reduced into small components using a fractionator 80 that has a cryogen source sprayed on the biomass and then a motorized chopping blade fractionalizes the biomass into tiny pieces for ease of lysing the cells. The fractionalized biomass is provided to a tank 82 that holds water or a suitable material such as ethanol or a solvent, for example. Water is preferred for its low cost and separation of oil is simple. The water from the tank flows through a computer-controlled valve 84 into a cavitator 86. The output of the cavitator 86 is fed back into the tank 82 which holds the output of the cavitator 86 and the cold new biomass from fractionator 80. Sensors 87 are provided to detect the level of oil in the tank 82 and if the level is above a predetermined level, the valve 85 is opened to provide the water/oil combination into an oil tank 88, where the water can be separated from the oil using techniques known to those skilled in the art.

The cavitator 86 has a specialized rotor with dead-ended cavities. Spinning creates low pressure at the cavity bottoms. The low pressure zones collapse releasing shockwaves. Cavitation is created in the cavities, not on metal surfaces. The cavitation is controlled, therefore there is no damage. The cavitation events induce highly energetic shock waves and corresponding highly intense and rapid pressure fluctuations that propagate through the mixture within the cavitation zone which liberates CBD, THC and other oils and compounds from the *cannabis* pieces within the mixture and these compounds become dissolved or entrained within the fluid of the mixture. Upon leaving the controlled cavitator, the mixture is provided back to the tank.

The tank can contain sensors for extracting samples of the treated fluid for testing. A processor reads the sensor output and control the valves and the motor. The valves allow the water to circulate or diverts the water/oil to the oil collection tank, for example.

In some embodiments, in which flow meter is included in sensing device, flow meter can include an in-line flow turbine sensor. A flow turbine sensor can include a rotor that is turned by a liquid force proportional to flow of the liquid in a flow direction. For example, liquid flow of the water causes a bladed turbine inside the flow meter to turn at an angular velocity directly proportional to the velocity of the liquid being monitored. As the blades pass beneath a magnetic pickup coil in the flow meter, a pulse signal is generated. For example, a Hall Effect sensor can be included that supplies pulses used for digital or analog signal processing. Each pulse can represent a discrete volume of liquid. A frequency of the pulse signal can be directly proportional to angular velocity of the turbine and the flow rate. A large number of pulses can provide high resolution. In other examples, flow meter can include an ultrasonic flow meter that determines time of flight measurement, an acoustic (Doppler) flow meter, or any other flow meter that can monitor flow of a substance and acquire flow data representing the flow. In a number of embodiments, the flow data measured by flow meter can be sent to controller using a flow data line. Other sensors include:

Turbidity Sensor—Turbidity sensors measure suspended solids in water, typically by measuring the amount of light transmitted through the water. They are used in river and stream gaging, wastewater and effluent measurement, drinking water treatment process and control, control instrumentation for settling ponds, sediment transport research, and laboratory measurements.

Conductivity Sensor—Conductivity measurements are carried out in industrial processes primarily to obtain information on total ionic concentrations (e.g. dissolved compounds) in aqueous solutions. Widely used applications are water purification, clean in place (CIP) control, and the measurement of concentration levels in solutions. The measuring system consists of an appropriate inline sensor directly inserted or in a housing, a cable connected to a transmitter converting the received signals to a measurement result or forwarding it to the processor. pH Sensor—pH is an important parameter to be measured and controlled. The pH of a solution indicates how acidic or basic (alkaline) it is. pH sensor components are usually combined into one device called a combination pH electrode. The measuring electrode is frequently glass and quite fragile.

ORP Sensor—ORP sensors measure the Oxygen-Reduction Potential of a solution. Used in tandem with a pH sensor, the ORP measurement provides insight into the level of oxidation/reduction reactions occurring in the solution.

The mixture may be circulated through the controlled cavitation a plurality of times until the extraction of CBD, THC and other oils and compounds is maximized. Alternatively, single pass treatment may well be acceptable in many instances. Subsequently, the remaining lignin from the hemp pieces is separated from the mixture and the CBD, THC and other oils and compounds, now dissolved or entrained within the fluid of the mixture, can be separated from the fluid of the mixture through standard techniques.

In one embodiment, the cavitation pump unit includes a motor, a shaft axially mounted on a motor shaft, a plurality of impellers disposed at a predetermined distance along a circumferential surface of the shaft, and a housing surrounding the shaft and the plurality of impellers. The plurality of impellers includes cutter parts each of which protrudes to be inclined toward an inner surface of the housing in one direction, and cavitation grooves recessed inward in directions facing each other are defined in both side surfaces of each of the cutter parts.

The processor with sensors determines and removes the oil once the oil concentration exceeds a threshold. Where the liquid is water, suitable separation techniques can be used to isolate oil from water, such as a boiler to boil off water, a centrifuge, or a nano filter to remove oil from the water. The system of FIG. 2 also can be used together with other extraction techniques to improve significantly the efficiency and yield of such techniques. The system of FIG. 2 can be arranged upstream of the traditional extraction system in a pre-treatment configuration or downstream of the traditional extraction system.

For example, the above system can be configured as a post-treatment system. After the traditional extraction system as extracted the CBD, THC and other compounds that it is capable of extracting, the resulting effluent is passed through the cavitator to remove remaining CBD, THC and other compounds from the *cannabis* plant material. Since much of the CBD, THC and other compounds are extracted in the traditional extraction system, it should take less time to extract remaining CBD, THC and other compounds using the cavitator and the compounds become dissolved or entrained in the fluid and can be separated later through known techniques.

In another embodiment, the trailer 50 can contain equipment that can be used for Live Resin Extraction. The *cannabis* or hemp is dried before it is processed. In live resin extraction, the live plant is frozen (such as with liquid nitrogen) right after it is harvested in order to perform extraction from a freshly-cut plant. A resin product is then created by using a closed-loop hydrocarbon extraction machine.

In a further embodiment, the system can be used for Cold trapping, which involves using a vacuum pumping system with a device known as a cold trap, which helps to remove contaminants. The system sublimates gas directly into a solid form, bypassing the liquid stage entirely. The product crystallizes in a sort of "frost" on the surface of the cold trap. The terpenes of the plant are equally as responsible as THC for the high experienced during use (perhaps even more so).

The system can also be used for Supercritical CO2 Extraction. Carbon dioxide is considered a "supercritical fluid" that becomes a liquid under pressure. In extractions, CO2 leaves no residue. The supercritical CO2 is put into a pressurized container with the *cannabis* material. The mixture is then put through a filter to separate the CO2 from the hemp or *cannabis* and, when the pressure in the system is released, the CO2 evaporates back into a gas. In one embodiment, the trailer 50 can perform CO2 extraction where highly pressurized carbon dioxide and varying temperatures are to extract CBD and other constituents. Sub-critical CO2 CBD extraction uses low pressure and low temperature. Supercritical CO2 CBD Extraction uses high pressure and extremely low temperature. Mid-critical uses high pressure and a variation of temperature which determines the number of terpenes that are preserved. The end result is a pure product—it is able to isolate the cannabinoids at 90 percent efficiency. In the supercritical CO2 extraction method, once the CO2 becomes liquid, the pressure and temperature are raised until the liquid becomes supercritical—it simultaneously adopts properties halfway between a gas and a liquid. The CO2 can then fill a container like a gas, but it maintains the density of a liquid. This keeps the extraction from damaging the final product, which makes it safe for human consumption. CBD oil that is extracted with the subcritical method tends to have more terpenes preserved than does CO2 oil extracted with the supercritical method; the latter requires Winterization, which is the process of removing the unwanted elements, such as lipids and waxes. Once extracted, the CBD oil is combined with 200-proof grain alcohol and is mixed thoroughly. Then it is placed in a freezer overnight. The next day, it is ready for filtration. After all the unwanted elements have been removed, the alcohol is also removed using heat.

In yet another embodiment, an ethanol CBD oil extraction with liquid nitrogen is used. The embodiment uses high-grain alcohol to remove the oil from the *cannabis*. This is done through a multi-step process which starts with mixing hemp with ethanol. Then, the solution is filtered and distilled until no ethanol remains and all that's left is a full-spectrum CBD oil. The process allows the solvent properties of Ethanol to extract useful substances, namely Cannabinoids, from the plant material. But, unwanted plant material, such as Chlorophyll or waxes, is extracted by the Ethanol as well. The extraction of unwanted plant material is due to the polar nature of Ethanol while the process occurs at temperatures exceeding 0 degrees C. Further purification, such as winterization, is required to remove the unwanted plant material, increasing the time, effort, and capital required to produce quality CBD or THC. As the temperature of the Ethanol decreases, the extraction of unwanted plant material also decreases. Once the temperature is below that of −60 degrees C., further purification becomes unnecessary. Thus, CBD or THC extraction with super-cooled Ethanol is extremely efficient. In this embodiment, the system keeps the Nitrogen in an extremely cold liquid condition throughout the entire heat exchanger to maintain the liquid Nitrogen's exceptional energy absorption capabilities. This is accomplished by using components that deliver extremely high flow cryogen: a high-pressure liquid Nitrogen source, a large cross-sectional flow path, a heat exchanger design, and a high-flow type solenoid valve. The heat exchanger designed for the increased viscosity of Ethanol in extremely low temperature conditions has such a design that limits the ability of the heat exchanger to trap the viscous Ethanol even with increased convection. An example of a heat exchanger with great ability to trap viscous Ethanol would be a typical heat exchanger where many fins are placed parallel to each other. Ethanol congeals between these fins and effectively decreases the surface area of the heat exchanger significantly, as well as limiting the heat transfer from the bulk of the Ethanol to the heat exchanger. An example of a heat exchanger with limited ability to trap congealed Ethanol would be one consisting of spiral tubing. Ethanol that does congeal on the surface of the heat exchanger isn't shielded from the liquid flow around it and cannot inhibit the heat exchangers ability to transfer heat from the Ethanol. The heat exchanger can trap congealed Ethanol.

Cryogenic Preservation of Farm Products

In another embodiment, instead of cooling the ethanol, the LN2 can be sprayed on the biomass to preserve quality and then transported the product at cryogenic (i.e., super-cooled) temperatures of less than −40 degrees C. Alternatively, the cryogenic cooler may be coupled to a container including product disposed at a super-frozen temperature and the combination shipped together to another location. In one embodiment, the cryogenic cooler may be used to provide high quality biomass from a first location (such as a point of harvest) to distinct second location. The cryogenic cooler is useful for providing a "super-frozen pipeline" (i.e., an essentially unbroken delivery chain of super-frozen product) from a point of freezing to a point of delivery. The apparatus is particularly useful in providing an essentially continuous delivery chain of biomass from a point of harvest to an end user (e.g., a distributor, wholesaler, retailer, or even a restaurant). For example, a forty-foot shipping container may be loaded with approximately 20 metric tons or more of hemp biomass at a first location and shipped to a second location (such as an extraction location). The super-frozen product may be stored for an indefinite time at the second location prior to being shipped to one or more third locations. The product may be shipped to the third locations in the same forty-foot container or in one or more smaller containers, such as but not limited to ISO LD3 containers. At the one or more third locations a cryogenic cooler may be interfaced to the shipping container to provide for automatic regulation of the super-frozen temperature in the interior thereof. This process may be repeated until the product is ultimately defrosted and/or consumed, e.g., at a supermarket, hotel, or restaurant.

Biomaterials Made from Post-Extraction Material

Figure 4:
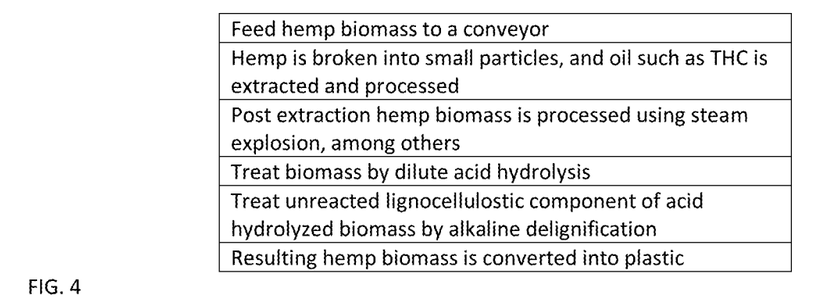
FIG. 4 shows an exemplary hemp bioplastic production process.

FIG. 4 shows an exemplary hemp bioplastic production process with the following operations:

Feed hemp biomass to a conveyor

Hemp is broken into small particles, and oil such as THC is extracted and processed Post extraction hemp biomass is processed using steam explosion, among others Treat biomass by dilute acid hydrolysis Treat unreacted lignocellulostic component of acid hydrolyzed biomass by alkaline delignification Resulting hemp biomass is converted into plastic.

In another embodiment, the post oil extraction biomass can be used for industrial applications. The previously chopped hemp mass by product from extraction is used as cellulose fragments and hydrophilic binders are embedded within the cellulose fragments. The combination is encapsulated with hydrophobic binders.

The hydrophilic binder can be partially hydrolysed polyvinyl acetate. Partially hydrolysed polyvinyl acetate is known by those skilled in the art to be a substantially hydrophilic polymer that readily forms micelles in water. The diameter and nature of the partially hydrolysed polyvinyl acetate particles is such that they locate within the cellulose fragment. The hydrophobic binder can be an epoxy resin. Cured epoxy resins are known by those skilled in the art to be hydrophobic in nature. The uncured epoxy resin is therefore formed into micelles with a typical diameter of ~0.5-2 μm. The diameter and nature of the epoxy particles is such that these particles cannot locate within the cellulose fragment. The epoxy encapsulates the cellulose fragments and hence the partially hydrolysed polyvinyl acetate located therein, so rendering the biocomposite material impermeable to water.

The first stage of this process involves the production of the cellulose fragments where the hemp plant material left over from the above process is recycled into board materials for industrial use. The coarsely chopped hemp is then hydrothermally treated, at a temperature between 85-120° C. at atmospheric pressure, until it begins to soften. Optionally steam and pressures above atmospheric pressures may be utilized to soften the hemp. The resultant cooking liquid is then drained off from the softened coarsely chopped hemp. Fresh water is then added to the residue material and this material is then processed in high speed blender for approximately 3-5 minutes so as to increase the available surface area of the material. Optionally, the material can then be immediately used as described below. Alternatively, the material can be allowed to stand for a period of time before use with or without the addition of a micro-organism e.g. bacteria or yeast. Such additional steps further assist in the breakdown of the hemp material. The resultant pulp produced by the blending process may then be filtered and washed with clean water. Next the residue Produced within the previous stage is mixed with a concentrated bleach solution and thereafter allowed to stand for 30 minutes, although longer time periods may be employed. The addition of bleach acts to kill of any unwanted micro-organisms while ensuring that a significant quantity of the pectins and hemicelluloses present within the original hemp material is dissolved within the resultant solution. The bleach is then removed by washing and filtering. Thereafter, water is added to the residue which is then homogenized by passing through a high shear in-line mixer or a high shear batch mixer. This involves the passing of the residue through a fine mesh under high shearing conditions so as to break down the cellular material in the residue so as to produce a pulp containing a range of cellulose fragments i.e. sized from individual cellulose microfibrils (on a scale of 20 nm in diameter) up to sections of cellulose cells typically 50 μm in length and breadth and less than 1 μm in thickness depending on the precise processing conditions. The process then reduces the water content within the resultant pulp. This is achieved by wrapping the pulp in a fine meshed bag and then pressing within a standard mechanical press. The resulting pressed pulp provides the required cellulose fragments and in particular comprises 1-30% cellulose by weight, and so behaves as a solid, feeling dry to the touch. It is essential that there remains enough water present within the cellulose fragments so as to prevent the cellulose fragments from interacting too strongly and therefore forming a rigid solid.

The byproducts of farming such as hemp fiber is used as reinforcement in composites. The blending materials range from thermoplastics such as polypropylene and polyethylene to thermoset fiber such as polyester. Plant based resins from soy, canola or corn can also used for a 100% biocomposite. Such biocomposites are used automotive interior substrates, furniture and other consumer products. Hemp fiber can be used to produce mineral based composites, in much the same way polypropylene or glass fiber is used to reinforce cement or plaster. The use of injection molding technology is also starting to gain ground using hemp fiber as a reinforcing material allowing hemp fiber to be used in more complex shapes and structures. The structures are tagged on the blockchain so the source of production through the supply chain is tracked.

In another aspect, composites that retain the natural antibacterial properties of hemp can be used to kill several types of surface bacteria including *E. coli*. Such products can be used in medical facilities, kitchen supplies, plant or calf toys, exercise mats etc.

The blending materials range from thermoplastics such as polypropylene and polyethylene to thermoset fiber such as polyester. Plant based resins from soy, canola or corn can also used for a 100% biocomposite. Such biocomposites are used automotive interior substrates, furniture and other consumer products. Hemp fiber can be used to produce mineral based composites, in much the same way polypropylene or glass fiber is used to reinforce cement or plaster. The use of injection molding technology is also starting to gain ground using hemp fiber as a reinforcing material allowing hemp fiber to be used in more complex shapes and structures. The structures are tagged on the blockchain so the source of production through the supply chain is tracked.

In other embodiments, the compositions and articles involve methylation of a lignin preparation followed by blending with various quantities (for example anywhere from 0 wt % to 25 wt %) of secondary, e.g., miscible polymeric, oligomeric and/or monomeric components. The process includes the following:

Feed hemp biomass to a conveyor

Hemp is chopped up, and oil such as THC is extracted and processed

Remaining chopped hemp biomass is processed using steam explosion, among others

Treat biomass by dilute acid hydrolysis

Treat unreacted lignocellulostic component of acid hydrolyzed biomass by alkaline delignification Resulting hemp biomass is converted into plastic For example, dried hemp plant/biomass is continuously loaded onto feed conveyor and into feed system that dispenses hemp biomass onto extraction belt conveyor at a set rate. Ethanol is pressurized and pumped through spray manifold above conveyor. This will directly spray onto the biomass to perform extraction. At the end of conveyor biomass and oil slurry will drain into semi enclosed bath with screw augers. Biomass is continuously metered out of bath with auger and into screw press to press out remaining ethanol and cannabinoids. Slurry is then metered out of bath and pumped through vacuum drum filter for particulate removal. Slurry is then pumped through filter press containing carbon depth filter sheets for pigment removal. Filtered slurry is stored in holding tank then metered into closed loop falling film evaporator to remove and recover ethanol from CBD crude oil.

The post-extraction slurry of hemp is composed of libriform fibers who are high lignin content. Steam explosion (SE) auto-hydrolysis is then done by saturated only steam without any additional reagents, usually at pressures 32 atmospheres to produce lignin without any dash. In the SE process, the biomass is treated by saturated steam, usually at pressures up to 40 bars. The treatment time varies from some seconds to some minutes. After the treatment, the biomass is decompressed (exploded) to the pressure of ambient atmosphere.

One embodiment uses a continuous, interwoven chain of several continuous stages. These may be generically recognized from the biomass ethanol, chemical pulping and separation process literature as including: (1) dilute acid hydrolysis; (2) alkaline delignification; (3) enzymatic hydrolysis; (4) fermentation; and (5) product separation.

One embodiment uses a five stage process, as follows: (1) dilute acid hydrolysis (hemicellulose); (2) dilute acid hydrolysis (cellulose); (3) alkaline delignification; (4) bacterial fermentation; and (5) yeast fermentation combined with enzymatic hydrolysis. In addition, this process also involves intertwined product separation and recovery and the recycling of useful process facilitators, such as water and enzymes. The acid presoaked biomass is spun dry, and then further dried by solar/waste heat to about 50% solids.

Stage 1—Dilute Acid Hydrolysis (Hemicellulose): the stage involves dilute acid hydrolysis of cellulosic polymer chains in the pre-treated lignocellulosic biomass feedstock, using strong acids, such as nitric or sulfuric. The result is to hydrolyze, solubilize and substantially convert to monomeric sugars most of the polysaccharide constituents of hemicellulose and a small portion, most easily hydrolyzed fraction of cellulose contained in the lignocellulosic feedstock material. Stage 1 of this embodiment involves dilute acid hydrolysis of the pre-treated biomass feedstock. Exemplary conditions for this hydrolysis are about 0.4% HNO3, at about 195° C. for about 5 minutes in a saturated steam environment within a pressure reactor such as is commonly employed in the pulping industry. Stage 1 is preferably terminated by rapid pressure release (steam explosion) and will solubilize and liberate about one-third of the material of the feedstock. The liquid hydrolysate and solids are then washed and pressed. Following the Stage 1 dilute acid hydrolysis, a first product separation and recovery is conducted. The Stage 1 liquid hydrolysate is washed and pressed repeatedly from the residual solids to recover about 95% of the liberated sugars, polysaccharide fragments and coproduct volatile organic compounds-such as acetic acid, furfural and hydroxymethylfurfural. The resulting press liquid comprising nominally six times the biomass feed contains solubilized product in about 5% concentration. The liquid is conveyed to a reservoir from which it is passed through nanofiltration (NF) membranes with a standard molecular weight cutoff designed to concentrate and contain the sugars. The concentrated retentate from the NF separation contains the free sugars at nominally 20% concentration and polysaccharide fragments, which are conveyed to the Stage 4 bacterial fermentation process, to be described. The NF permeate contains volatile organics, along with dilute acid catalyst. Importantly, the economics of the process may be enhanced by recycling the permeate back through the Stage 1 wash cycles in successive iterations of the process, conserving acid and accumulating and concentrating VOC coproducts prior to their recovery.

Stage 2—Dilute Acid Hydrolysis (Cellulose)—The lignin/cellulose solids from the press of stage 1 are passed to Stage 2, a second dilute acid hydrolysis stage. To the solids are added 2% acid (e.g., nitric (HNO3) (preferred), sulfuric or hydrocloric) at about 210° C. for about 7 minutes in a saturated steam environment within a pressure reactor. This more rigorous dilute acid hydrolysis is effective to disrupt the cellulose bonds following the more moderate conditions of Stage 1 which are effective to disrupt the more easily hydrolyzed hemicellulose. Like Stage 1, Stage 2 is preferably terminated by rapid pressure release (steam explosion) and will solubilize and liberate about half of the material from the Stage 1 press. The hydrolysate and solids are then washed and pressed to about 50% solids. Following the Stage 2 dilute acid hydrolysis, a further product separation and recovery is conducted. The Stage 2 liquid hydrolysate is washed and pressed repeatedly from the residual solids to recover about 95% of the liberated sugars, oligosaccharide fragments, acid and additional coproduct volatile organic compounds-such as hydroxymethylfurfural. As in Stage 1, the resulting press liquid is conveyed to a reservoir from which it is passed through nanofiltration (NF) membranes. The concentrated retentate from the NF separation contains the free sugars at nominally 20% concentration and polysaccharide and oligosaccharide fragments, which together are conveyed to the Stage 4 bacterial fermentation process, to be described. Through the nanofiltration process on the Stage 1 and 2 hydrolysates separation of the depolymerized sugar and oligosaccharide (polymer fragment) from the stream of the process is facilitated. The aqueous permeate of nanofiltration is effectively reconcentrated by vacuum distillation for recycling the acid catalyst to the hydrolysis process stages. Importantly, the reconcentrated catalyst will also be recognized to contain the solubilized fraction of volatile organic chemicals that are liberated by the hydrolysis process in approximately 5% concentration weight/weight at each step of the biomass processing. Thus, after several steps of processing, recovering and concentrating the catalyst carrier and VOCs, a substantial accumulation of VOC products is effected in the catalyst. When this accumulation is judged cost effective to recover, the VOCs may be extracted by fractional distillation, as noted above.

Stage 3—Alkaline Delignification of the lignocellulosic solids from the press of Stage 2.

Chemistries of the pulp and paper industry that have not previously been integrated with acid dehydrolysis and used in connection with the processing of lignocellulostic biomass are adopted. The preferred embodiment for environmental benefits adopts sulfur-free alkaline delignification from so-called "alkaline pulping" chemistry. Stage 2 solids may be combined with about 4% strong base (such as alkali or other lignin-dissolving base) at about 210° C. for about 4 minutes. The alkaline process may be effectively catalyzed by the use of accelerators such as anthraquinone and tetrahydroanthraquinone. In processes in accordance with the present invention, as distinct from the classical pulping application, the prior removal of most of the hemicellulose and a major cellulose fraction, with steam explosion to disruptively expand the fiber matrix before delignification, serves both to preserve chemical value of easily degraded hemicellulose while rendering very accessible to pulping chemicals the lignin component of the plant cell walls within the exposed fiber matrix. Further, important interpolymeric chemical bonds are obviated in the dilute acid hydrolysis, solubilization and removal of the cellulosic chemicals. The major result is that lignins are solubilized and washed out of the thus highly disrupted, porous fiber matrix in a characteristic time of minutes rather than hours, as in conventional (wood) pulping.

In a process using classical chemical pulping theory, the time constant for delignification decreases (e.g., in kraft pulping) by about a factor of two for each 8° C. increase in temperature. Such rapid temporal performance in delignification as provided here is jointly facilitated by choosing to operate toward the higher end of the temperature range, here also employed in dilute acid hydrolysis, with similarly rapid solubilization and extraction of the hemicellulose. Stage 3 may selectively be terminated by either steam explosion or more energy, conserving heat recovery decompression. The product of this stage is then washed and pressed to separate the soluble lignin from the remaining lignin/cellulose solids. The introduced alkaline delignification stage importantly distinguishes a process in accordance with the present invention from the common practice of biomass ethanol technology involving only dilute acid pretreatment and enzymatic hydrolysis. As shown in testing of pretreated solids in recycle reactor enzymatic hydrolysis, the presence of naturally occurring amounts of lignin with the cellulose in the enzyme recycle reactor results in major, noneconomic declines in enzyme productivity (from cycle to cycle of enzyme reuse against fresh substrate.

Lignin-based thermoplastics have adjustable mechanical properties over the range identified with polyethylene, polypropylene and polystyrene are, moreover, biodegradeable. The plastics may be foamed, filmed, cast or extrusion- or injection-molded to satisfy a great variety of applications. To the extent that the polymeric backbone for a lignin-based plastic already exists, energy-intensive synthesis reactions and associated sources of chemical toxicity are avoided. Rather, as taught by Sarkanen, the production of the new plastic only requires a catalytic chemical reaction, e.g., methylation, at normal conditions of temperature and pressure. Thus, there are multiple capital and operations cost savings available in its production. Stage 3 washed solids residue may be fed back to Stage 2 for subsequent further dilute acid hydrolysis and Stage 3 alkaline delignification to thereby achieve near 100% substrate conversion.

Stages 4 and 5-Fermentation—The concentrated hydrolysate sugars and oligosaccharides of Stages I and II are combined and the glucose and five-carbon sugars are fermented with *Zymomonas mobilis* bacterium in a Stage 4 continuous-flow cascade recycle reactor, blocking and recycling the bacterial catalyst at the outflow while the residual six-carbon sugars and oligosaccharides are passed through a microfilter to a second (yeast) fermenter, discussed below. The ethanol and carbon dioxide products are separated and the remaining six-carbon sugars and oligosaccharides are concentrated by vacuum evaporative distillation from the Stage 4 fermentation reactor. Complete hydrolysis of the oligosaccharides and fermentation of the residual six-carbon sugars occurs in a Stage 5 continuous-flow simultaneous saccharification and fermentation (SSF) recycle reactor with cellulase enzyme and *Saccharomyces cerevisiae* yeast catalyst (combined yeast fermentation/enzymatic hydrolysis). Separation of ethanol and capture of fermentation $CO_2$ by vacuum evaporative distillation from the SSF reactor is conducted. In Stages 4 and 5 of the process, bacterial fermentation of sugars, also takes place in a continuous recycle reactor comprised of vessels containing separately or jointly provision of biocatalytic agents for fermenting both the five- and six-carbon sugars liberated in Stages 1, 2 and 3 of the process. The practice of Stages 4 and 5 is distinct from prior art in biomass ethanol technology in achieving very high yield with large gains in productivity in both time and tankage realized by: 1) implementing a continuous-flow reactor with feedstock replenishment and product extraction, while 2) employing microfiltration to retain biocatalyst in the reactor to speed the process and 3) optionally making provision for product extracting dilution water to control end-product inhibition in the fermentation process. In the case of the continuously fed SSF enzyme recycle reactor, a nanofiltration membrane can be used to retain catalyst and concentrated sugars in the reactor, while passing residual aqueous carrier.

Product Separation and Extraction—Separation of the VOC coproducts can be conducted by fractional distillation from the accumulated concentrated VOCs of the Stages 1 and 2 hydrolysate (wash) filter permeate. At VOC harvesting, the residual acid may be neutralized with ammonia or other suitable base to produce, along with other residual mineral salts, a valuable nitrogen-rich fertilizer coproduct. The use of an NF membrane in the Stage 5 reactor to retain concentrated sugars while accumulating the organic chemical products of hydrolysis represents the beginning of the last instance of intertwined product separation in the process. Those familiar with the art of biomass ethanol technology will recognize that the provisions for high product recovery and separation as provided for the products of Stage 1 dilute acid hydrolysis also synergistically serve to obviate a well-known, important source (acetic acid) of inhibition of the activity of fermentation organisms. The provision of the process to employ filtration to separate the diluted volatile organic chemicals from the resulting concentrated sugars prior to fermentation is a further important advance of the process of the present invention over previous processes. The product separation and extraction of the process is then concluded with product separation and recovery through fractional distillation from the higher boiling solvent. The solvent so depleted of product is then conservatively recycled back through the solvent extraction process to recover more volatile organic product. The fact that the solvent is chosen both to be buoyant and insoluble in water allows the product-laden solvent to be readily separated from the water on the one hand and, on the other, the product extraction dilution water to be recycled substantially free of solvent back through the fermentation recycle reactor.

What is claimed is:
1. A method for extracting oil from a biomass, comprising:
    applying a cryogen to a tank to render brittle the biomass;
    reducing the cryogenically frozen biomass to small portions;

placing the reduced cryogenically frozen biomass in the tank filled with a liquid;

generating shock waves and pressure variations with cavitation;

applying the shock waves and pressure variations to a mixture formed from the liquid and the reduced cryogenically frozen biomass with oil dissolved or entrained within a fluid of the mixture; and extracting oil from the fluid.

2. The method of claim 1, comprising extracting full spectrum tetrahydrocannabinol (THC) or cannabidiol (CBD) from the fluid.

3. The method of claim 1, comprising detecting elevated temperature in the mixture and applying the cryogen to the liquid to cool the mixture.

4. The method of claim 1, comprising sensing an oil concentration in the fluid.

5. The method of claim 4, comprising harvesting the oil once the oil concentration exceeds a threshold.

6. The method of claim 1, wherein the liquid comprises ethanol, and wherein the extracting oil comprises extracting tetrahydrocannabinol (THC) or cannabidiol (CBD) and cryogenic cooling the mixture with LN2 or CO2.

7. The method of claim 1, comprising converting a post oil extractions biomass into a bioplastic or a biocomposite material.

8. The method of claim 1, comprising converting a post oil extraction biomass into a building material.

9. The method of claim 1, wherein the liquid comprises water or a solvent.

10. The method of claim 1, wherein after extraction, further comprising:

reducing the biomass into small fragments and extracting oil therefrom with post-extraction biomass;

processing the post-extraction biomass using steam explosion;

treating the post-extraction biomass by dilute acid hydrolysis;

treating unreacted lignocellulostic component of acid hydrolyzed post-extraction biomass by alkaline delignification; and generating bio-plastic from the post-extraction biomass.

* * * * *